April 25, 1939. G. E. ALEXANDER Plant Pat. 328

NECTARINE

Filed Sept. 6, 1938

INVENTOR

*Geo. E. Alexander*

ATTORNEY

Patented Apr. 25, 1939

Plant Pat. 328

UNITED STATES PATENT OFFICE

328

NECTARINE

George Edward Alexander, Venice, Calif., assignor to Karl K. Snyder, Hughson, and A. D. Di Grazia, San Francisco, Calif.

Application September 6, 1938, Serial No. 228,691

1 Claim. (Cl. 47—62)

This invention or discovery relates in general to nectarines, and in particular is directed to a nectarine tree and its fruit of the cream fleshed and free stone type.

The nectarine tree herein described was discovered in the year 1929 as a seedling growing near Hughson, in the county of Stanislaus, California, and since its discovery the variety has been successfully asexually reproduced and found to have the same distinctive characteristics as the original tree. Approximately 1000 trees of such new variety have been propagated on the Snyder ranch near Hughson, California, since 1932, and the fruit from such trees was first introduced to the trade and favorably received in the year 1937.

The variety of nectarine tree, hereinafter described in detail, is distinctive by reason of the fact that the fruit is of exceptionally large size, a reddish purple color in its substantial entirety, thick and tough skinned, firm of flesh and well flavored, and keeps in storage longer than other varieties of nectarines.

Figure 1:
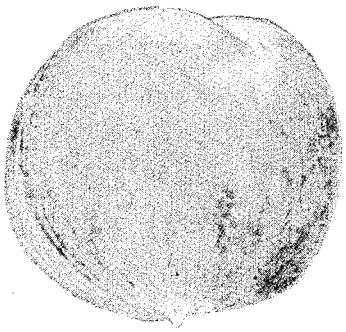
Figure 2:
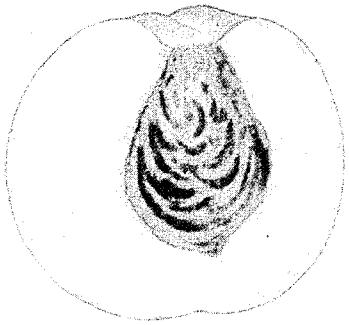

In the drawing, Fig. 1 is a perspective view of the whole fruit and Fig. 2 is a longitudinal section of the same, but with the stone intact.

The following description sets forth the details of the new and distinct variety of nectarine tree and its fruit:

*Tree.*—The tree is of medium size and strength, upright, dense, vase formed and hardy. It is a productive and regular bearer. The trunk is of medium size and smoothness, and the branches are likewise of medium size and smoothness. Trees budded from the new variety make a rather slow seasonal growth, but the branches develop a a large amount of fruit wood and the twigs grow close together with closely set buds. The new growth changes from a green to reddish purple color very early, and the bark of wood two years old is a dark brown. Thus mature trees can be easily distinguished from peach and nectarine trees of other varieties.

*Leaves.*—The leaves are medium size, lanceolate, and acutely pointed, while being of medium thickness, dark green color and smooth. The leaves average four to five inches in length, and one to one and one-half inches in width. The leaves are of a glandular type with finely serrated edges, the petiole being of medium length and thickness. The glands average two in number, are disposed nearly opposite, and are of medium size, while being disposed very close to the stem. The stipules are prominent.

*Flower buds and flowers.*—The flower buds are closely set, hardy, of medium size and length, and plump. The flowers begin to bloom on or about April 1st and usually are in full bloom by April 15th; the flowers being late as compared with other varieties of nectarines. The flowers are of medium size and deep pink in color.

*Fruit.*—The fruit at the time the jacket falls is oval shaped with a sharp point at the pistil end, and in maturity the fruit is variable, unsymmetrical and globose in form; the average size of the mature fruit being approximately 2¼ inches axially, and approximately 2⅜ inches transversely in the suture plane. The suture is an inconspicuous line, while the ventral surface is slightly rounded; the cavity being slightly elongated in the suture plane with the suture showing on one side. The cavity is approximately ½ inch deep and ¾ inch in breadth. The base is rounded, while the apex is rounded and depressed. The pistil point is oblique. The stem is of medium size, glabrous, and its adherence to the stone is weak.

The skin of the fruit is thick, tough, sour tenacious to the flesh, and has a slight tendency to crack. When the jacket falls, the skin rapidly changes from a green to a reddish, mottled purple, and in its substantial entirety; the color of the skin when the fruit is ripe resembling the color of the Satsuma plum. Down is wanting.

The flesh of the fruit is a whitish cream mottled with red next to the skin, and the surface of the pit cavity is slightly red, with white fibers. Amygdalin is wanting. The flesh ripens evenly and the texture is fine and melting, the fibers tender, the flavor subacid to mild, and the aroma distinct.

The stone is free and adheres to the flesh over its entire surface. The fibers are short and are retained like threads along the ridges of the stone. The stone is small in size; being approximately 1⅛ inches long, 1 inch in breadth, and ⅝ inch in thickness. The form of the stone is oblong; its base straight and hilum narrow; the sides being equal and the surface regularly furrowed near base. The stone is pitted from the base to above center. The ridges are rounded. The pits are elongated with wing toward base. The dorsal edge is narrow with deep groove to above center, and the ridges are interrupted. The color of the stone is brown tinged with red, and the stone has little tendency to split.

*Ripening period.*—In an average season, the fruit is first picked on or about August 12th and continues to about September 1st.

*Use.*—The eating and keeping qualities of the fruit are excellent, and the fruit may be used for shipping, canning or drying, and may be kept in storage longer than other varieties of nectarines.

As compared with other varieties of nectarines and particularly the Gower variety, the above described variety of nectarine matures for picking at a later date, is larger, is more completely colored (being a reddish purple in its substantial entirety), is thicker skinned and better flavored, and has a firm flesh.

The above described characteristics are of course typical and may be subject to certain variations as all varieties of fruit differ among themselves in adaption to a particular region, soil, or climatic conditions.

Having thus described my invention, what I claim as new and useful and desire to secure by Letters Patent is:

The herein described variety of nectarine tree bearing a fruit which is characterized by its large size, the reddish purple color in its substantial entirety when ripe, its thick and tough skin, its firm well flavored flesh, and its long keeping quality in storage.

GEORGE EDWARD ALEXANDER.